United States Patent [19]
Lechleiter

[11] Patent Number: 5,472,434
[45] Date of Patent: Dec. 5, 1995

[54] SPIKE RETAINER SYSTEM

[75] Inventor: Robert J. Lechleiter, Pompton Plains, N.J.

[73] Assignee: Akzo N.V., Arnhem, Netherlands

[21] Appl. No.: 61,031

[22] Filed: May 14, 1993

[51] Int. Cl.⁶ .................................................... A61M 5/32
[52] U.S. Cl. ........................ 604/280; 604/263; 604/283; 604/411; 604/414; 604/905
[58] Field of Search .................. 604/56, 82–92, 604/411–415, 905, 263, 280, 283; 128/912; 141/285, 383; 285/399, 921

[56] References Cited

U.S. PATENT DOCUMENTS

| | | |
|---|---|---|
| D. 267,199 | 12/1982 | Koenig . |
| 1,522,198 | 1/1925 | Marcy . |
| 4,607,671 | 8/1986 | Aalto et al. ............................ 604/413 |
| 4,787,898 | 11/1988 | Raines ................................... 604/411 |
| 4,878,900 | 11/1989 | Sundt . |
| 4,895,570 | 1/1990 | Larkin ................................... 604/411 |
| 4,927,423 | 5/1990 | Malmborg . |
| 4,950,260 | 8/1990 | Bonaldo . |
| 4,969,879 | 11/1990 | Lichte . |
| 4,991,629 | 2/1991 | Ernesto et al. . |
| 4,998,925 | 3/1991 | Al-Sioufi et al. . |
| 5,078,703 | 1/1992 | Bryant . |
| 5,100,394 | 3/1992 | Dudar et al. . |
| 5,120,324 | 6/1992 | Sancoff . |
| 5,137,524 | 8/1992 | Lynn et al. . |
| 5,147,324 | 9/1992 | Skakoon et al. . |
| 5,156,598 | 10/1992 | Skakoon et al. . |

FOREIGN PATENT DOCUMENTS

| | | | |
|---|---|---|---|
| 8002502 | 11/1980 | WIPO | 604/415 |
| 8601712 | 3/1986 | WIPO | 604/413 |

Primary Examiner—Randall L. Green
Assistant Examiner—P. Zuttarelli

[57] ABSTRACT

A device for use in securing a venting pin or infusion spike to a delivery container such as a vial or bottle particularly when instilling a medicinal fluid to a patient through an intravenous set, catheter or similar fluid delivery set.

13 Claims, 4 Drawing Sheets

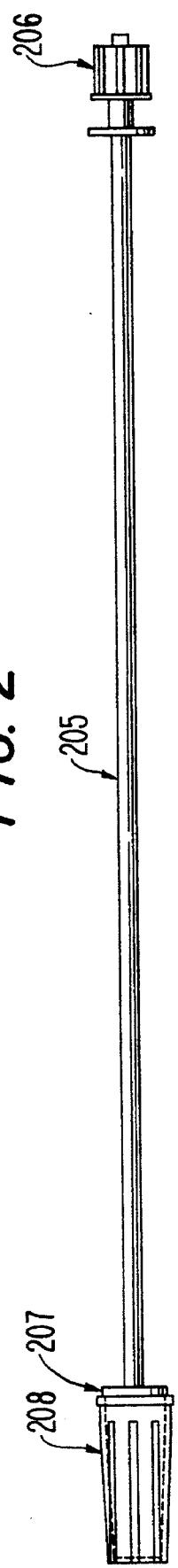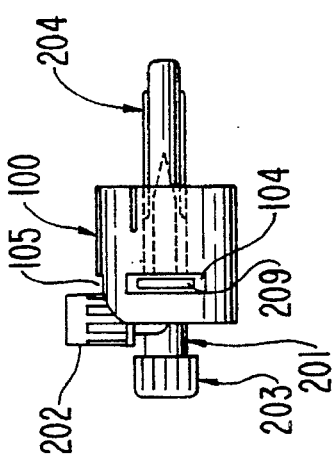

SPIKE RETAINER SYSTEM

BACKGROUND OF THE INVENTION

1. Field of the Invention

The present invention relates generally to the field of medical devices, and in particular to a device for use in securing a vented piercing pin or infusion spike to a vial or bottle when instilling a medicinal fluid to a patient through an intravenous set, catheter or similar fluid delivery set.

2. Background Information

Current intravenous sets and instillation attachments which employ a vented piercing pin or infusion spike do not lock to the fluid container and may be inadvertently detached by movement of a patient or other action. This can result in spillage of fluid, improper delivery and possible physical jeopardy.

The present invention was therefore developed to provide a simple and efficient solution to these problems. The present invention secures a standard piercing pin or spike to a vial and overcomes these problems.

SUMMARY OF THE INVENTION

In order to solve the above-mentioned problems, the present invention provides the following novel features and advantages.

According to an embodiment of the invention, the device for use in securing a vented piercing pin or infusion spike to a delivery container such as a vial or bottle particularly when instilling a medicinal fluid to a patient through an intravenous set, catheter or similar fluid delivery set, includes a body having a cylindrical shape. The body includes a plurality of radial slots spaced around the circumference of the body for expanding when assembling the device onto a delivery container. At least two ports are disposed on opposite sides of the body for accommodating infusion spike or venting pin flanges. The device further includes an inwardly extending lip portion for engaging a delivery container seal.

One advantage in using the present invention in combination with venting pins and infusion spikes lies in the snug and secure attachment to an inverted delivery container, e.g., vial or bottle, by virtue of the inwardly extending lip or undercut and the expansion slots.

In a further embodiment, the device body is made of an injection molded thermoplastic. The device is thus inexpensive and easy to manufacture by standard injection molding techniques. In a further embodiment, the injection molded thermoplastic comprises polypropylene.

In a further embodiment, the plurality of radial slots comprises six equally spaced radial slots disposed around the circumference of one end of the body to allow for expansion of the end during assembly of the device onto the delivery container. Six equidistant slots was found to provide adequate expansion and ease of use with standard sized vials, however, the optimum number of slots and spacing for a given application of the invention may vary and can be empirically determined.

In a further embodiment of the device, the plurality of ports comprises two opposed circumferentially extending lateral ports disposed on an end of the body for accommodating standard infusion spike or venting pin flanges. Standard spikes or venting pins generally have two flanges extending in opposite directions laterally, and thus, this embodiment accommodates this standard configuration. The invention may, however, be modified to accommodate other configurations of flanges by providing ports in different locations as is appropriate, without departing from the scope of the invention as set forth in the appended claims. The ports with flanges extended therethrough, advantageously prevent inadvertent separation of the infusion spike or venting pin from the device.

In another embodiment, the plurality of ports further comprise a cutout portion for accommodating an air inlet filter of a vented piercing pin device. A standard type of vented piercing pin device includes an air inlet filter which extends from the device, and thus, this embodiment accommodates such a configuration.

The spike retainer according to the present invention may be advantageously used as part of a complete set including the spike retainer, air inlet filter, spike guard, vented piercing pin, tubing and catheter adapter. Thus, medical personnel are provided with all the accessories needed to perform instilling procedures in one kit.

These and other objects and aspects of the invention are better understood with reference to the detailed description and accompanying drawings, and it will be understood that changes in the specific structure shown and described may be made within the scope of the claims without departing from the spirit of the invention.

BRIEF DESCRIPTION OF THE DRAWINGS

FIG. 2 shows an embodiment of the present invention as part of a set including the spike retainer, air inlet filter, spike guard, vented piercing pin, tubing and catheter adapter;

DETAILED DESCRIPTION OF THE PREFERRED EMBODIMENTS

Figure 1:
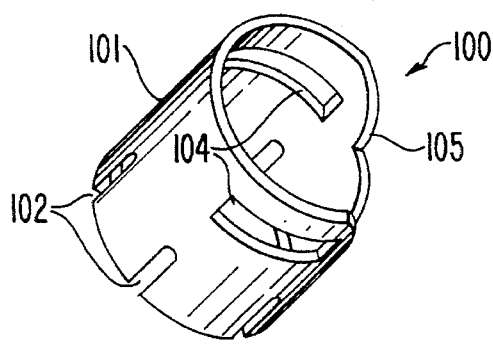
FIG. 1 is a drawing showing a perspective view of a preferred embodiment of the invention.
Figure 1A:
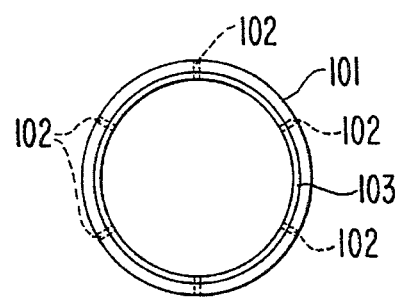
FIGS. 1a, 1b and 1c, show an end view and two side views respectively of the preferred embodiment.
Figure 1B:
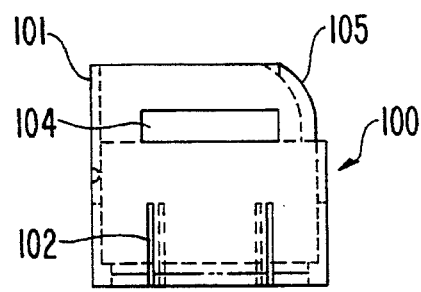
Figure 1C:
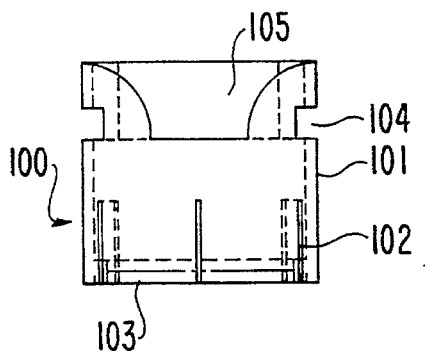

The invention will now be described in more detail by example with reference to the embodiments shown in the Figures. It should be kept in mind that the following described embodiments are only presented by way of example and should not be construed as limiting the inventive concept to any particular physical configuration.

With reference to FIGS. 1, 1a, 1b and 1c, a preferred embodiment of the spike retainer device 100 is illustrated having a generally cylindrically shaped body 101. This particular shape is designed to fit standard delivery containers which have generally round seals and necks. However, the invention is susceptible to modification in size and shape to accommodate other configurations of delivery containers, e.g., having oval, or rectangular shaped seals and necks, and such modifications are considered to be within the scope of the appended claims. Since the device 100 is advantageously formed of an injection molded thermoplastic material, modifications can be accomplished with changes in the shape of the mold used to manufacture the device, as would be readily apparent to one skilled in the art.

The illustrated embodiment of the device 100 features a plurality of radial slots 102, e.g., six slots preferably spaced equidistant around the circumference of the body 101, to provide for expansion when assembling the device 100 onto the neck over the sealed end of a delivery container. A snug fit is thereby achieved between the device 100 and the delivery container. An inwardly extending lip or undercut 103 (see FIG. 1a) is provided in order for the spike retainer device 100 to securely grip the neck of a delivery container and prevent inadvertent detachment.

The illustrated embodiment of the device 100 also features ports 104 disposed on sides of the body 101 to accommodate infusion spike or venting pin flanges. In a preferred embodiment, the upper end of the device 100 includes two opposed lateral slots 104 to accommodate standard infusion spike or venting pin flanges. A cutout portion 105 is also provided (best seen in FIG. 1c) which accommodates an air inlet filter of a vented piercing pin.

The ports 104 with flanges extended therethrough, advantageously prevent inadvertent separation of the infusion spike or venting pin from the device 100.

These features of the device 100 advantageously permit the secure attachment of a venting pin or infusion spike to an inverted vial or bottle when instilling a medicinal fluid through an intravenous system, catheter or other fluid delivery system.

In a preferred embodiment, the lower end of the device 100 includes six radial slots 102 equally spaced around the circumference of the body 101 to allow for expansion of the lower end of the body 101 when the device 100 is assembled onto the neck of a vial or other delivery container, and provide a snug fit. In the preferred embodiment, in order for the spike retainer to securely grip the neck of a delivery container, the lower end also includes an inwardly extending lip portion or undercut 103. An expansion of the radial slots 102 occurs upon engaging the retainer 100 onto a delivery container seal. Once in place over the seal, the device 100 essentially returns to its unassembled profile and the lip portion or undercut 103 prevents inadvertent detachment. The inwardly extending lip portion or undercut 103 is provided because the slotted body 101 alone might not provide sufficient gripping to secure the device 100 to the delivery container.

The inwardly extending lip portion or undercut 103, advantageously engages under, for example, a 20 mm vial seal when assembled thereto, and retains the device 100 securely intact. Thus a significant advantage of the device 100 is obtained, i.e., to "lock" a spike onto a vial. Use of a spike without retainer device 100 might otherwise result in inadvertent detachment and leakage during delivery of a drug.

FIG. 2 shows the device 100 as part of an instillation set. The spike retainer device 100 is shown assembled to a mini-spike dispensing assembly including vented piercing pin 201 with air inlet filter 202, female luer lock cover 203, and mini-spike guard 204. The set also includes a 9" length of instillation tubing 205 with spin-lock II assembly 206, luer catheter adapter 207 and 3/16" adapter cap 208. As is shown, the air inlet filter 202 of the vented piercing pin 201 advantageously fits in cutout portion 105 of the device 100.

One of the flanges 209 of the piercing pin 201 is visible extending through lateral port 104 of the device 100. On the opposite side of the device 100, although not visible from this view, the other flange of the piercing pin 201 extends through a port of the device 100 in the same manner.

Figure 3:
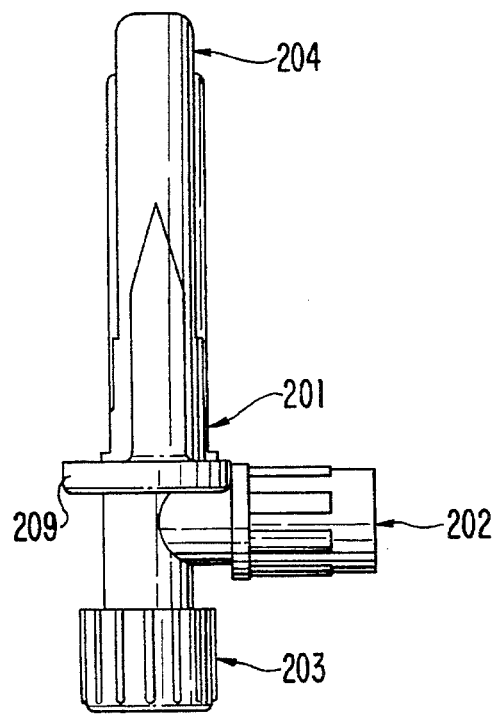
FIG. 3 shows the mini-spike dispensing pin assembly of the set of FIG. 2.
Figure 4:
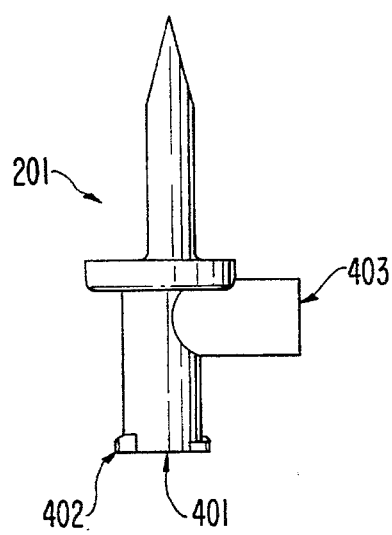
FIG. 4 shows the vented piercing pin of the set of FIG. 2.
Figure 5:
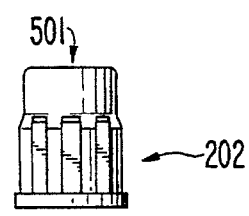
FIG. 5 shows the air inlet filter assembly of the set of FIG. 2.
Figure 6:
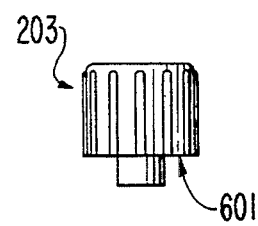
FIG. 6 shows the female non-vented luer lock cover of the set of FIG. 2.
Figure 7:
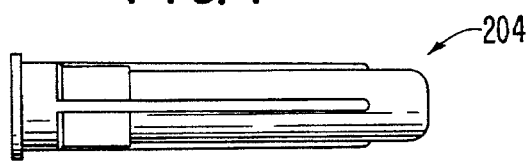
FIG. 7 shows the mini-spike guard of the set of FIG. 2.
Figure 8:
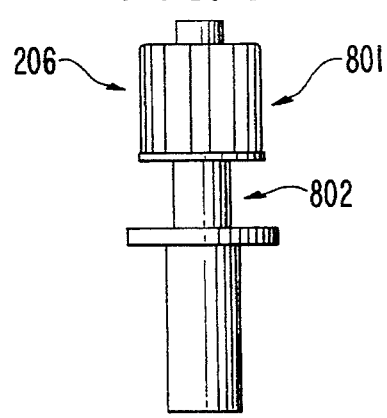
FIG. 8 shows the spin-lock assembly of the set of FIG. 2.
Figure 9:
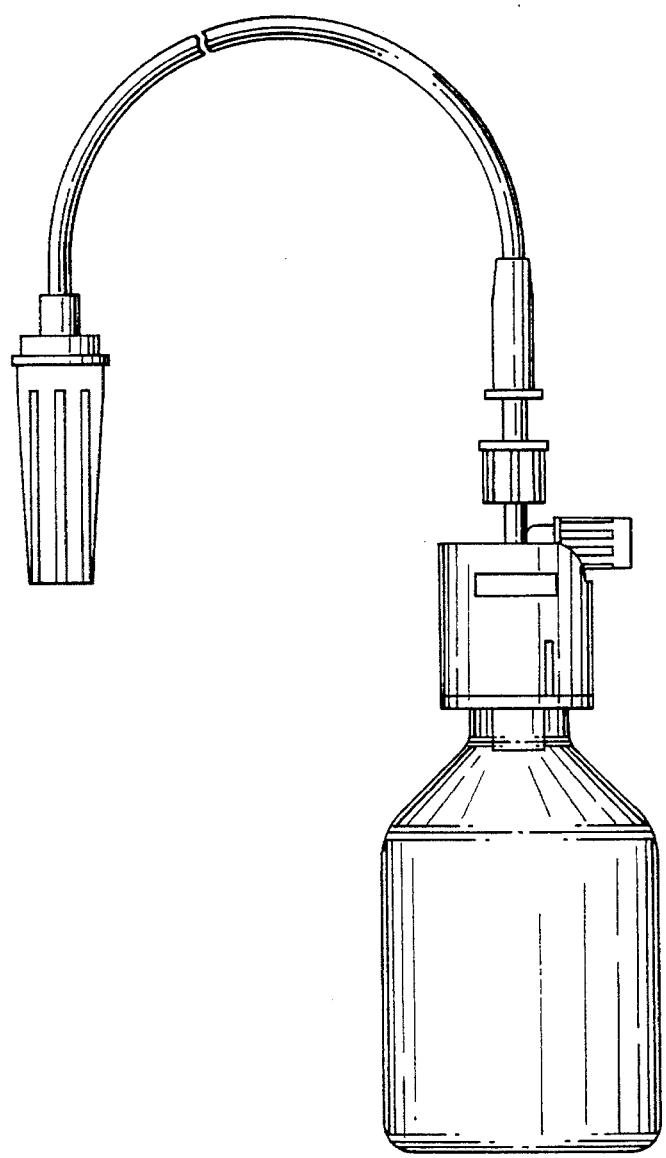
FIG. 9 shows the set of FIG. 2 assembled onto a standard delivery container.
Figure 10:
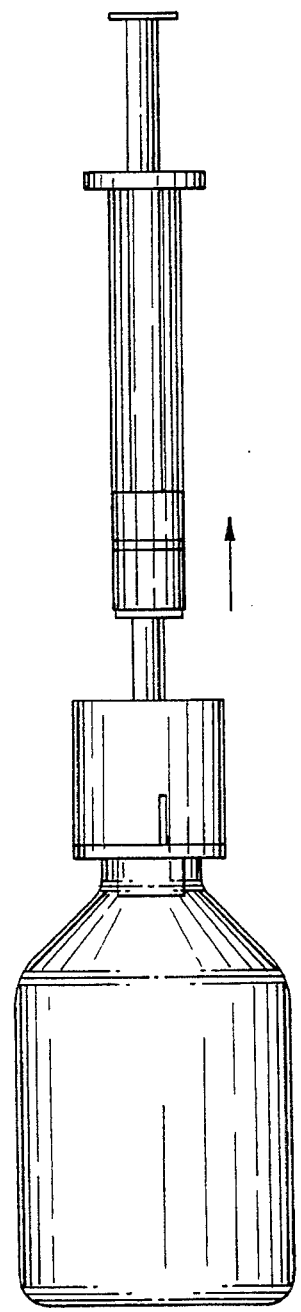
FIG. 10 shows an embodiment of the present invention being used with a standard delivery container and a syringe.

FIG. 3 shows the mini-spike dispensing assembly of FIG. 2 enlarged and in more detail, including vented piercing pin 201, air inlet filter 202, female luer lock cover 203, and mini-spike guard 204. FIG. 4 is an enlarged drawing of the vented piercing pin 201 itself, illustrating female luer taper 401, luer lock ears 402 and female luer taper 403. FIG. 5 shows air inlet filter 202 enlarged, including filter disk 501. FIG. 6 shows the female luer lock cover 203 enlarged, including luer lock threads 601. FIG. 7 shows mini-spike guard 204 in profile, and FIG. 8 shows spin-lock II assembly 206 enlarged and in more detail, including male luer lock fitting (rotating collar) 801 and floating collar 802.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

For example, a device 100 of a given size could be used with virtually any delivery tube neck size provided the tube is fitted with a matching sized adapter or fitment, and is not therefore limited to use with the disclosed standard sizes.

The disclosed embodiment may be modified to accommodate other configurations of flanges by providing ports in different locations as is appropriate, without departing from the scope of the invention as set forth in the appended claims. The disclosed embodiment is also susceptible to modification in size and shape to accommodate other configurations of delivery containers, e.g., having oval, or rectangular shaped seals and necks, and such modifications are considered to be within the scope of the appended claims.

Although, in the preferred embodiment, the device body is made of an injection molded thermoplastic, in particular, polypropylene, other suitable materials may be used as would be readily apparent to one skilled in the art. Furthermore, although a preferred embodiment includes six equally spaced expansion slots, a larger or a smaller number could be used to adapt the device to a particular application. If the device is not for use with a vented piercing pin having an air inlet filter, the cutout portion for accommodating the air inlet filter may, of course, be eliminated.

What is claimed:

1. An apparatus for use in securing a piercing device having flanges to a delivery container such as a vial or bottle particularly when instilling a medicinal fluid into a patient through an intravenous set, catheter or similar fluid delivery set, said apparatus comprising:

a cylindrical body having an axis, first and second ends, and inner and outer cylindrical surfaces extending between the first and second ends, the outer cylindrical surface having a circumference, said cylindrical body including:

a plurality of axially extending slots spaced around the circumference of the cylindrical body at the first end thereof, for expanding when assembling the apparatus onto the delivery container, at least two ports, each extending between the inner and outer cylindrical surfaces of the cylindrical body at the second end thereof, and extending circumferentially partly around said cylindrical body, for fittingly engaging the piercing device flanges, and an inwardly extending lip portion disposed at the first end of the cylindrical body, for fittingly engaging a delivery container seal.

2. The apparatus according to claim 1, wherein the plurality of axial slots comprises six axial slots disposed equidistantly around the circumference of the first end of the cylindrical body to allow for expansion of the first end during assembly of the apparatus onto the delivery container.

3. The apparatus according to claim 1, wherein said cylindrical body is made of an injection molded thermoplastic.

4. The apparatus according to claim 3, wherein the injection molded thermoplastic comprises polypropylene.

5. The apparatus according to claim 1, wherein the at least two ports comprises two opposed circumferentially extending lateral ports disposed at the second end of the cylindrical body for fittingly engaging the piercing device flanges.

6. The apparatus according to claim 5, wherein the cylindrical body further comprises a cutout portion for receiving an air inlet filter of the piercing device therethrough.

7. The apparatus according to claim 6, wherein the apparatus is used as part of a set comprising the apparatus, an air inlet filter, a spike guard, a vented piercing pin, a length of tubing and a catheter adapter, thereby providing medical personnel with accessories needed to perform instilling procedures.

8. An apparatus for use in securing a piercing device having flanges to a delivery container such as a vial or bottle particularly when instilling a medicinal fluid into a patient through an intravenous set, catheter or similar fluid delivery set, said apparatus comprising:

an outer peripheral wall;

first means for fittingly engaging an end of the delivery container, including first securing means for securing the apparatus to the delivery container, and expanding means for expanding during assembly of the apparatus onto the delivery container; and second means for fittingly engaging the piercing device, including aperture means extending entirely through the outer peripheral wall for securing the piercing device to the apparatus by receiving the flanges of the piercing device therein.

9. An apparatus for use in securing a piercing device having flanges to a delivery container such as a vial or bottle particularly when instilling a medicinal fluid into a patient through an intravenous set, catheter or similar fluid delivery set, said apparatus comprising:

first means for fittingly engaging an end of the delivery container, including first securing means for securing the apparatus to the delivery container, and expanding means for expanding during assembly of the apparatus onto the delivery container; and second means for fittingly engaging the piercing device, including second securing means for securing the piercing device to the apparatus by receiving the flanges of the piercing device therein, said second means further including first cutout means for receiving an air inlet filter of the piercing device therethrough.

10. In a method of instilling a medicinal fluid to a patient through a fluid delivery set, the improvement comprising securing a piercing device having a flange to a delivery container utilizing an apparatus having a cylindrical body having an axis, first and second ends, and inner and outer cylindrical surfaces extending between the first and second ends, the outer cylindrical surface having a circumference, said cylindrical body including:

a plurality of axially extending slots spaced around the circumference of the cylindrical body at the first end thereof, for expanding when assembling the apparatus onto the delivery container, at least two ports, each extending between the inner and outer cylindrical surfaces of the cylindrical body at the second end thereof, and extending circumferentially partly around said cylindrical body, for fittingly engaging a flange of the piercing device, and an inwardly extending lip portion disposed at the first end of the cylindrical body, for fittingly engaging a delivery container seal, wherein the piercing device is a vented piercing pin.

11. In a method of instilling a medicinal fluid to a patient through a fluid delivery set, the improvement comprising securing a piercing device having a flange to a delivery container utilizing an apparatus having a cylindrical body having an axis, first and second ends, and inner and outer cylindrical surfaces extending between the first and second ends, the outer cylindrical surface having a circumference, said cylindrical body including:

a plurality of axially extending slots spaced around the circumference of the cylindrical body at the first end thereof, for expanding when assembling the apparatus onto the delivery container, at least two ports, each extending between the inner and outer cylindrical surfaces of the cylindrical body at the second end thereof, and extending circumferentially partly around said cylindrical body, for fittingly engaging a flange of the piercing device and an inwardly extending lip portion disposed at the first end of the cylindrical body, for fittingly engaging a delivery container seal, wherein the piercing device is an infusion spike.

12. The improvement according to claim 11 wherein said fluid delivery set is an intravenous set.

13. The improvement according to claim 11 wherein said fluid delivery set is a catheter.

* * * * *

UNITED STATES PATENT AND TRADEMARK OFFICE
CERTIFICATE OF CORRECTION

PATENT NO.   : 5,472,434
DATED        : December 5, 1995
INVENTOR(S)  : Robert J. Lechleiter It is certified that error appears in the above-indentified patent and that said Letters Patent is hereby corrected as shown below:

Column 2, line 32, please delete "FIG. 2 shows" and replace with -- FIGS. 2 and 2a show --.

Column 3, line 59, please delete "FIG. 2 shows" and replace with -- FIGS. 2 and 2a show --.

Signed and Sealed this

Twenty-eighth Day of May, 1996

Attest:

BRUCE LEHMAN

*Attesting Officer*   *Commissioner of Patents and Trademarks*